United States Patent
Wurst et al.

[11] Patent Number: 6,130,045
[45] Date of Patent: Oct. 10, 2000

[54] THERMOSTABLE POLYMERASE

[75] Inventors: Helmut Wurst, Cupertino; Zhi-Hao Qiu, San Jose, both of Calif.

[73] Assignee: Clontech Laboratories, Inc., Palo Alto, Calif.

[21] Appl. No.: 09/096,399

[22] Filed: Jun. 11, 1998

[51] Int. Cl.[7] ..................................................... C12Q 1/68
[52] U.S. Cl. .............................. 435/6; 536/23.1; 435/183
[58] Field of Search ........................ 435/6, 183; 536/23.1

[56] References Cited

U.S. PATENT DOCUMENTS

| | | | |
|---|---|---|---|
| H1531 | 5/1996 | Blumentals et al. | 435/194 |
| 4,889,818 | 12/1989 | Gelfand et al. | 435/194 |
| 5,079,352 | 1/1992 | Gelfand et al. | 536/27 |
| 5,108,892 | 4/1992 | Burke et al. | 435/6 |
| 5,352,600 | 10/1994 | Gelfand et al. | 435/194 |
| 5,405,774 | 4/1995 | Abramsom et al. | 435/252.3 |
| 5,436,149 | 7/1995 | Barnes | 435/194 |
| 5,455,170 | 10/1995 | Abramsom et al. | 435/252.3 |
| 5,466,591 | 11/1995 | Abramsom et al. | 435/194 |
| 5,556,772 | 9/1996 | Sorge et al. | 435/91.2 |
| 5,616,494 | 4/1997 | Barnes | 435/252.3 |
| 5,674,738 | 10/1997 | Abramsom et al. | 435/252.3 |

FOREIGN PATENT DOCUMENTS

| | | |
|---|---|---|
| 0 482 714 B1 | 4/1996 | European Pat. Off. |
| 92/06200 | 4/1992 | WIPO |
| 95/14782 | 6/1995 | WIPO |
| 96/38568 | 12/1996 | WIPO |
| 97/24444 | 7/1997 | WIPO |

*Primary Examiner*—Scott W. Houtteman
*Attorney, Agent, or Firm*—Bozicevic, Field & Francis; Bret Field

[57] ABSTRACT

A thermostable enzyme having polymerase activity and substantially no nuclease activity is provided. The thermostable enzyme is characterized by comprising a sequence of nine amino acid residues at least proximal to the N-terminus that has less than 50% but greater than 40% amino acid sequence identity with residues 280 to 288 of the naturally occurring *Thermus aquaticus* polymerase. The subject enzyme finds use in a variety of different application in which polynucleotides are enzymatically produced, particularly in PCR based applications.

37 Claims, 4 Drawing Sheets

FIG. 1

```
gaattccatg agggggcacg agtccggcct tcaggaaagc cccaaggccc tggaggaggc      60
cccctggccc ccgccggaag gggccttcgt gggctttgtg ctttcccgca aggagcccat     120
gtgggccgat cttctggccc tggccgccgc caggggggc cgggtccacc gggcccccga      180
gccttataaa gccctcaggg acctgaagga ggcgcggggg cttctcgcca aagacctgag     240
cgttctggcc ctgagggaag gccttggcct cccgccggc gacgacccca tgctcctcgc      300
ctacctcctg gacccttcca acaccacccc gagggggtg gcccggcgct acggcgggga      360
gtggacggag gaggcggggg agcgggccgc cctttccgag aggctcttcg ccaacctgtg     420
ggggaggctt gaggggagg agaggctcct ttggctttac cgggaggtgg agaggcccct     480
ttccgctgtc ctggcccaca tggaggccac gggggtgcgc ctggacgtgg cctatctcag     540
ggccttgtcc ctggaggtgg ccgaggagat cgcccgcctc gaggccgagg tcttccgcct     600
ggccggccac cccttcaacc tcaactcccg ggaccagctg gaaagggtcc tctttgacga     660
gctagggctt cccgccatcg gcaagacgga aagaccggc aagcgctcca ccagcgccgc      720
cgtcctggag gccctccgcg aggcccaccc catcgtggag aagatcctgc agtaccggga     780
gctcaccaag ctgaagagca cctacattga ccccttgccg gacctcatcc accccaggac     840
gggccgcctc cacacccgct caaccagac ggccacgcc acgggcaggc taagtagctc      900
cgatcccaac ctccagaaca tccccgtccg caccccgctt gggcagagga tccgccgggc     960
cttcatcgcc gaggaggggt ggctattggt ggccctggac tatagccaga tagagctcag    1020
ggtgctggcc cacctctccg gcgacgagaa cctgatccgg gtcttccagg aggggcggga    1080
catccacacg gagaccgcca gctggatgtt cggcgtcccc cgggaggccg tggacccct     1140
gatgcgccgg gcggccaaga ccatcaactt cggggtcctc tacggcatgt cggcccaccg    1200
cctctcccag gagctagcca tcccttacga ggaggcccag gccttcattg agcgctactt    1260
tcagagcttc cccaaggtgc gggcctggat tgagaagacc ctggaggagg caggaggcg     1320
ggggtacgtg gagaccctct cggccgccg ccgctacgtg ccagacctag aggcccgggt    1380
gaagagcgtg cgggaggcgg ccgagcgcat ggccttcaac atgcccgtcc agggcaccgc    1440
cgccgacctc atgaagctgg ctatggtgaa gctcttcccc aggctggagg aaatgggggc    1500
caggatgctc cttcaggtcc acgacgagct ggtcctcgag gccccaaaag agagggcgga    1560
ggccgtggcc cggctggcca aggaggtcat ggagggggtg tatcccctgg ccgtgccct     1620
ggaggtggag gtggggatag gggaggactg gctctccgcc aaggagtgat accacctcta    1680
ga                                                                   1682
```

(SEQ ID NO:01)

FIG. 2

```
            M RGHESGLQES PKALEEAPWP PPEGAFVGFV LSRKEPMWAD LLALAAARGG  330
   RVHRAPEPYK ALRDLKEARG LLAKDLSVLA LREGLGLPPG DDPMLLAYLL DPSNTTPEGV  390
   ARRYGGEWTE EAGERAALSE RLFANLWGRL EGEERLLWLY REVERPLSAV LAHMEATGVR  450
   LDVAYLRALS LEVAEEIARL EAEVFRLAGH PFNLNSRDQL ERVLFDELGL PAIGKTEKTG  510
   KRSTSAAVLE ALREAHPIVE KILQYRELTK LKSTYIDPLP DLIHPRTGRL HTRFNQTATA  570
   TGRLSSSDPN LQNIPVRTPL GQRIRRAFIA EEGWLLVALD YSQIELRVLA HLSGDENLIR  630
   VFQEGRDIHT ETASWMFGVP REAVDPLMRR AAKTINFGVL YGMSAHRLSQ ELAIPYEEAQ  690
   AFIERYFQSF PKVRAWIEKT LEEGRRRGYV ETLFGRRRYV PDLEARVKSV REAAERMAFN  750
   MPVQGTAADL MKLAMVKLFP RLEEMGARML LQVHDELVLE APKERAEAVA RLAKEVMEGV  810
   YPLAVPLEVE VGIGEDWLSA KE                                          832
```

(SEQ ID NO:02)†

†Numeration is based on the amino acid sequence of Taq polymerase.

FIG. 3

```
atgaccatga ttacgaattc catgaggggg cacgagtccg gccttcagga aagccccaag      60
gccctggagg aggcccctg gcccccgccg aagggcct tcgtgggctt tgtgctttcc         120
cgcaaggagc ccatgtgggc cgatcttctg gccctggccg ccgccagggg gggccgggtc     180
caccgggccc ccgagcctta taaagccctc agggacctga aggaggcgcg ggggcttctc      240
gccaaagacc tgagcgttct ggccctgagg aaggccttg gcctcccgcc cggcgacgac      300
cccatgctcc tcgcctacct cctggaccct tccaacacca ccccgagggg ggtggcccgg     360
cgctacggcg gggagtggac ggaggaggcg ggggagcggg ccgccctttc cgagaggctc     420
ttcgccaacc tgtggggag gcttgagggg gaggagaggc tcctttggct ttaccgggag      480
gtggagaggc cctttccgc tgtcctggcc cacatggagg ccacgggggt gcgcctggac      540
gtggcctatc tcagggcctt gtccctggag gtggccgagg agatcgcccg cctcgaggcc     600
gaggtcttcc gcctggccgg ccaccccttc aacctcaact cccgggacca gctggaaagg     660
gtcctctttg acgagctagg gcttcccgcc atcggcaaga cggagaagac cggcaagcgc     720
tccaccagcg ccgccgtcct ggaggccctc cgcgaggccc accccatcgt ggagaagatc      780
ctgcagtacc gggagctcac caagctgaag agcacctaca ttgacccctt gccggacctc     840
atccacccca ggacgggccg cctccacacc cgcttcaacc agacggccac ggccacgggc      900
aggctaagta gctccgatcc caacctccag aacatccccg tccgcacccc gcttgggcag     960
aggatccgcc gggccttcat cgccgaggag gggtggctat ggtggccct ggactatagc      1020
cagatagagc tcagggtgct ggcccaccct tccggcgacg agaacctgat ccgggtcttc     1080
caggagggc gggacatcca cacggagacc gccagctgga tgttcggcgt ccccgggag      1140
gccgtggacc cctgatgcg ccggcggcc aagaccatca acttcggggt cctctacggc      1200
atgtcggccc accgcctctc ccaggagcta gccatccctt acgaggaggc ccaggccttc     1260
attgagcgct actttcagag cttcccccaag gtgcgggcct ggattgagaa gaccctggag    1320
gagggcagga ggcggggta cgtggagacc ctcttcggcc gccgccta cgtgccagac       1380
ctagaggccc gggtgaagag cgtgcgggag gcggccgagc gcatggcctt caacatgccc     1440
gtccagggca ccgccgccga cctcatgaag ctggctatgg tgaagctctt ccccaggctg    1500
gaggaaatgg gggccaggat gctccttcag gtccacgacg agctggtcct cgaggcccca    1560
aaagagaggg cggaggccgt ggcccggctg gccaaggagg tcatggaggg ggtgtatccc    1620
ctggccgtgc ccctggaggt ggaggtgggg ataggggagg actggctctc cgccaaggag    1680
tgataccacc tctaga                                                       1696
(SEQ ID NO:03)
```

FIG. 4

```
        TMITNSM RGHESGLQES PKALEEAPWP PPEGAFVGFV LSRKEPMWAD LLALAAARGG  330
        RVHRAPEPYK ALRDLKEARG LLAKDLSVLA LREGLGLPPG DDPMLLAYLL DPSNTTPEGV  390
        ARRYGGEWTE EAGERAALSE RLFANLWGRL EGEERLLWLY REVERPLSAV LAHMEATGVR  450
        LDVAYLRALS LEVAEEIARL EAEVFRLAGH PFNLNSRDQL ERVLFDELGL PAIGKTEKTG  510
        KRSTSAAVLE ALREAHPIVE KILQYRELTK LKSTYIDPLP DLIHPRTGRL HTRFNQTATA  570
        TGRLSSSDPN LQNIPVRTPL GQRIRRAFIA EEGWLLVALD YSQIELRVLA HLSGDENLIR  630
        VFQEGRDIHT ETASWMFGVP REAVDPLMRR AAKTINFGVL YGMSAHRLSQ ELAIPYEEAQ  690
        AFIERYFQSF PKVRAWIEKT LEEGRRRGYV ETLFGRRRYV PDLEARVKSV REAAERMAFN  750
        MPVQGTAADL MKLAMVKLFP RLEEMGARML LQVHDELVLE APKERAEAVA RLAKEVMEGV  810
        YPLAVPLEVE VGIGEDWLSA KE                                          832
        (SEQ ID NO:04)†
```

†Numeration is based on the amino acid sequence of Taq polymerase.

SEQUENCE LISTING

<160> NUMBER OF SEQ ID NOS: 4

<210> SEQ ID NO 1
<211> LENGTH: 1682
<212> TYPE: DNA
<213> ORGANISM: Artificial Sequence
<220> FEATURE:
<223> OTHER INFORMATION: Recombinantly engineered mutant

<400> SEQUENCE: 1

```
gaattccatg aggggcacg agtccggcct tcaggaaagc cccaaggccc tggaggaggc      60 ccctggcc ccgccggaag gggccttcgt gggctttgtg ctttcccgca aggagcccat     120
gtgggccgat cttctggccc tggccgccgc caggggggc cgggtccacc gggcccccga    180
gccttataaa gccctcaggg acctgaagga ggcgcgggg cttctcgcca aagacctgag    240
cgttctggcc ctgagggaag gccttggcct cccgcccggc gacgacccca tgctcctcgc    300
ctacctcctg gacccttcca acaccacccc cgaggggtg gcccggcgct acggcgggga    360
gtggacggag gaggcggggg agcggccgc cctttccgag aggctcttcg ccaacctgtg    420
ggggaggctt gaggggagg agaggctcct ttggctttac cgggaggtgg agaggcccct    480
ttccgctgtc ctggcccaca tggaggccac ggggtgcgc ctggacgtgg cctatctcag    540
ggccttgtcc ctggaggtgg ccgaggagat cgcccgcctc gaggccgagg tcttccgcct    600
ggccggccac cccttcaacc tcaactcccg ggaccagctg gaaagggtcc tctttgacga    660
gctagggctt cccgccatcg gcaagacgga gaagaccggc aagcgctcca ccagcgccgc    720
```

```
cgtcctggag gccctccgcg aggcccaccc catcgtggag aagatcctgc agtaccggga     780
gctcaccaag ctgaagagca cctacattga ccccttgccg acctcatcc accccaggac      840 gggccgcctc cacacccgct tcaaccgac ggccacggcc acgggcaggc taagtagctc      900
cgatcccaac ctccagaaca tccccgtccg caccccgctt gggcagagga tccgccgggc    960
cttcatcgcc gaggaggggt ggctattggt ggccctggac tatagccaga tagagctcag    1020
ggtgctggcc cacctctccg cgacgagaa cctgatccgg gtcttccagg agggcggga     1080 catccacacg gagaccgcca gctggatgtt cggcgtcccc cgggaggccg tgaccccct      1140 gatgcgccgg gcggccaaga ccatcaactt cggggtcctc tacggcatgt cggcccaccg    1200
cctctcccag gagctagcca tcccttacga ggaggcccag gccttcattg agcgctactt    1260
tcagagcttc cccaaggtgc gggcctggat tgagaagacc ctggaggagg caggaggcg    1320 ggggtacgtg gagaccctct tcggccgccg ccgctacgtg ccagacctag aggcccgggt    1380
gaagagcgtg cgggaggcgg ccgagcgcat ggccttcaac atgcccgtcc agggcaccgc    1440
cgccgacctc atgaagctgg ctatggtgaa gctcttcccc aggctggagg aaatgggggc    1500
caggatgctc cttcaggtcc acgacgagct ggtcctcgag gccccaaaag agaggcgga    1560 ggccgtggcc cggctggcca aggaggtcat ggaggggtg tatcccctgg ccgtgcccct    1620
ggaggtggag gtggggatag gggaggactg gctctccgcc aaggagtgat accacctcta   1680
ga                                                                    1682

<210> SEQ ID NO 2
<211> LENGTH: 553
<212> TYPE: PRT
<213> ORGANISM: Artificial Sequence
<220> FEATURE:
<223> OTHER INFORMATION: Recombinantly engineered mutant

<400> SEQUENCE: 2

Met Arg Gly His Glu Ser Gly Leu Gln Glu Ser Pro Lys Ala Leu Glu
  1               5                  10                  15

Glu Ala Pro Trp Pro Pro Glu Gly Ala Phe Val Gly Phe Val Leu
             20                  25                  30

Ser Arg Lys Glu Pro Met Trp Ala Asp Leu Leu Ala Leu Ala Ala Ala
         35                  40                  45

Arg Gly Gly Arg Val His Arg Ala Pro Glu Pro Tyr Lys Ala Leu Arg
     50                  55                  60

Asp Leu Lys Glu Ala Arg Gly Leu Leu Ala Lys Asp Leu Ser Val Leu
 65                  70                  75                  80

Ala Leu Arg Glu Gly Leu Gly Leu Pro Pro Gly Asp Asp Pro Met Leu
                 85                  90                  95

Leu Ala Tyr Leu Leu Asp Pro Ser Asn Thr Thr Pro Glu Gly Val Ala
                100                 105                 110

Arg Arg Tyr Gly Gly Glu Trp Thr Glu Glu Ala Gly Glu Arg Ala Ala
            115                 120                 125

Leu Ser Glu Arg Leu Phe Ala Asn Leu Trp Gly Arg Leu Glu Gly Glu
        130                 135                 140

Glu Arg Leu Leu Trp Leu Tyr Arg Glu Val Glu Arg Pro Leu Ser Ala
145                 150                 155                 160

Val Leu Ala His Met Glu Ala Thr Gly Val Arg Leu Asp Val Ala Tyr
                165                 170                 175

Leu Arg Ala Leu Ser Leu Glu Val Ala Glu Glu Ile Ala Arg Leu Glu
                180                 185                 190
```

```
Ala Glu Val Phe Arg Leu Ala Gly His Pro Phe Asn Leu Asn Ser Arg
            195                 200                 205

Asp Gln Leu Glu Arg Val Leu Phe Asp Glu Leu Gly Leu Pro Ala Ile
210                 215                 220

Gly Lys Thr Glu Lys Thr Gly Lys Arg Ser Thr Ser Ala Ala Val Leu
225                 230                 235                 240

Glu Ala Leu Arg Glu Ala His Pro Ile Val Glu Lys Ile Leu Gln Tyr
                245                 250                 255

Arg Glu Leu Thr Lys Leu Lys Ser Thr Tyr Ile Asp Pro Leu Pro Asp
                260                 265                 270

Leu Ile His Pro Arg Thr Gly Arg Leu His Thr Arg Phe Asn Gln Thr
                275                 280                 285

Ala Thr Ala Thr Gly Arg Leu Ser Ser Ser Asp Pro Asn Leu Gln Asn
            290                 295                 300

Ile Pro Val Arg Thr Pro Leu Gly Gln Arg Ile Arg Arg Ala Phe Ile
305                 310                 315                 320

Ala Glu Glu Gly Trp Leu Leu Val Ala Leu Asp Tyr Ser Gln Ile Glu
                325                 330                 335

Leu Arg Val Leu Ala His Leu Ser Gly Asp Glu Asn Leu Ile Arg Val
                340                 345                 350

Phe Gln Glu Gly Arg Asp Ile His Thr Glu Thr Ala Ser Trp Met Phe
                355                 360                 365

Gly Val Pro Arg Glu Ala Val Asp Pro Leu Met Arg Arg Ala Ala Lys
            370                 375                 380

Thr Ile Asn Phe Gly Val Leu Tyr Gly Met Ser Ala His Arg Leu Ser
385                 390                 395                 400

Gln Glu Leu Ala Ile Pro Tyr Glu Glu Ala Gln Ala Phe Ile Glu Arg
                405                 410                 415

Tyr Phe Gln Ser Phe Pro Lys Val Arg Ala Trp Ile Glu Lys Thr Leu
                420                 425                 430

Glu Glu Gly Arg Arg Arg Gly Tyr Val Glu Thr Leu Phe Gly Arg Arg
            435                 440                 445

Arg Tyr Val Pro Asp Leu Glu Ala Arg Val Lys Ser Val Arg Glu Ala
450                 455                 460

Ala Glu Arg Met Ala Phe Asn Met Pro Val Gln Gly Thr Ala Ala Asp
465                 470                 475                 480

Leu Met Lys Leu Ala Met Val Lys Leu Phe Pro Arg Leu Glu Glu Met
                485                 490                 495

Gly Ala Arg Met Leu Leu Gln Val His Asp Glu Leu Val Leu Glu Ala
            500                 505                 510

Pro Lys Glu Arg Ala Glu Ala Val Ala Arg Leu Ala Lys Glu Val Met
            515                 520                 525

Glu Gly Val Tyr Pro Leu Ala Val Pro Leu Glu Val Glu Val Gly Ile
            530                 535                 540

Gly Glu Asp Trp Leu Ser Ala Lys Glu
545                 550

<210> SEQ ID NO 3
<211> LENGTH: 1696
<212> TYPE: DNA
<213> ORGANISM: Artificial Sequence
<220> FEATURE:
<223> OTHER INFORMATION: Recombinantly engineered mutant
```

-continued

```
<400> SEQUENCE: 3
atgaccatga ttacgaattc catgagggggg cacgagtccg gccttcagga agccccaag      60 gccctggagg aggcccctg gccccgccg aagggggcct tcgtgggctt tgtgctttcc     120
cgcaaggagc ccatgtgggc cgatcttctg ccctggccg ccgccagggg gggccgggtc    180
caccgggccc ccgagcctta taaagccctc agggacctga aggaggcgcg ggggcttctc    240
gccaaagacc tgagcgttct ggccctgagg aaggccttg gcctcccgcc cggcgacgac    300 ccatgctcc tcgcctacct cctggaccct ccaacacca ccccgagggg ggtggcccgg    360
cgctacggcg gggagtggac ggaggaggcg ggggagcggg ccgccctttc cgagaggctc    420
ttcgccaacc tgtgggggag gcttgagggg aggagaggc tcctttggct ttaccgggag    480
gtggagaggc ccctttccgc tgtcctggcc cacatggagg ccacggggt gcgcctggac    540 gtggcctatc tcagggcctt gtccctggag gtggccgagg agatcgcccg cctcgaggcc    600
gaggtcttcc gcctggccgg ccaccccttc aacctcaact cccgggacca gctggaaagg    660
gtcctctttg acgagctagg gcttcccgcc atcggcaaga cggagaagac cggcaagcgc    720
tccaccagcg ccgccgtcct ggaggccctc cgcgaggccc accccatcgt ggagaagatc    780
ctgcagtacc gggagctcac caagctgaag agcacctaca ttgacccctt gccggacctc    840 atccaccccca ggacgggccg cctccacacc cgcttcaacc agacgccac ggccacgggc    900 aggctaagta gctccgatcc caacctccag aacatcccg tccgcacccc gcttgggcag    960
aggatccgcc gggccttcat cgccgaggag gggtggctat tggtgccct ggactatagc   1020 cagatagagc tcagggtgct ggcccacctc tccggcgacg agaacctgat ccgggtcttc   1080
caggaggggg gggacatcca cacggagacc gccagctgga tgttcggcgt ccccccgggag   1140 gccgtggacc ccctgatgcg ccgggcggcc aagaccatca acttcggggt cctctacggc   1200
atgtcggccc accgcctctc ccaggagcta gccatccctt acgaggaggc ccaggccttc   1260
attgagcgct actttcagag cttccccaag gtgcgggcct ggattgagaa gaccctggag   1320
gagggcagga ggcggggta cgtggagacc ctcttcggcc gccgccgcta cgtgccagac   1380
ctagaggccc gggtgaagag cgtgcgggag gcggccgagc gcatggcctt caacatgccc   1440
gtccagggca ccgccgccga cctcatgaag ctggctatgg tgaagctctt ccccaggctg   1500
gaggaaatgg gggccaggat gctccttcag gtccacgacg agctggtcct cgaggcccca   1560
aaagagaggg cggaggccgt ggcccggctg gccaaggagt catggagggg ggtgtatccc   1620
ctggccgtgc ccctggaggt ggaggtgggg atagggagg actggctctc cgccaaggag   1680
tgataccacc tctaga                                                  1696
```

<210> SEQ ID NO 4
<211> LENGTH: 559
<212> TYPE: PRT
<213> ORGANISM: Artificial Sequence
<220> FEATURE:
<223> OTHER INFORMATION: Recombinantly engineered mutant

<400> SEQUENCE: 4

```
Thr Met Ile Thr Asn Ser Met Arg Gly His Glu Ser Gly Leu Gln Glu
  1               5                  10                  15

Ser Pro Lys Ala Leu Glu Glu Ala Pro Trp Pro Pro Glu Gly Ala
                 20                  25                  30

Phe Val Gly Phe Val Leu Ser Arg Lys Glu Pro Met Trp Ala Asp Leu
             35                  40                  45
```

```
Leu Ala Leu Ala Ala Ala Arg Gly Gly Arg Val His Arg Ala Pro Glu
     50                  55                  60

Pro Tyr Lys Ala Leu Arg Asp Leu Lys Glu Ala Arg Gly Leu Leu Ala
 65                  70                  75                  80

Lys Asp Leu Ser Val Leu Ala Leu Arg Glu Gly Leu Gly Leu Pro Pro
                 85                  90                  95

Gly Asp Asp Pro Met Leu Leu Ala Tyr Leu Leu Asp Pro Ser Asn Thr
                100                 105                 110

Thr Pro Glu Gly Val Ala Arg Arg Tyr Gly Gly Glu Trp Thr Glu Glu
            115                 120                 125

Ala Gly Glu Arg Ala Ala Leu Ser Glu Arg Leu Phe Ala Asn Leu Trp
130                 135                 140

Gly Arg Leu Glu Gly Glu Arg Leu Leu Trp Leu Tyr Arg Glu Val
145                 150                 155                 160

Glu Arg Pro Leu Ser Ala Val Leu Ala His Met Glu Ala Thr Gly Val
                165                 170                 175

Arg Leu Asp Val Ala Tyr Leu Arg Ala Leu Ser Leu Glu Val Ala Glu
                180                 185                 190

Glu Ile Ala Arg Leu Glu Ala Glu Val Phe Arg Leu Ala Gly His Pro
            195                 200                 205

Phe Asn Leu Asn Ser Arg Asp Gln Leu Glu Arg Val Leu Phe Asp Glu
210                 215                 220

Leu Gly Leu Pro Ala Ile Gly Lys Thr Glu Lys Thr Gly Lys Arg Ser
225                 230                 235                 240

Thr Ser Ala Ala Val Leu Glu Ala Leu Arg Glu Ala His Pro Ile Val
                245                 250                 255

Glu Lys Ile Leu Gln Tyr Arg Glu Leu Thr Lys Leu Lys Ser Thr Tyr
            260                 265                 270

Ile Asp Pro Leu Pro Asp Leu Ile His Pro Arg Thr Gly Arg Leu His
            275                 280                 285

Thr Arg Phe Asn Gln Thr Ala Thr Ala Thr Gly Arg Leu Ser Ser Ser
290                 295                 300

Asp Pro Asn Leu Gln Asn Ile Pro Val Arg Thr Pro Leu Gly Gln Arg
305                 310                 315                 320

Ile Arg Arg Ala Phe Ile Ala Glu Glu Gly Trp Leu Leu Val Ala Leu
                325                 330                 335

Asp Tyr Ser Gln Ile Glu Leu Arg Val Leu Ala His Leu Ser Gly Asp
                340                 345                 350

Glu Asn Leu Ile Arg Val Phe Gln Glu Gly Arg Asp Ile His Thr Glu
            355                 360                 365

Thr Ala Ser Trp Met Phe Gly Val Pro Arg Glu Ala Val Asp Pro Leu
370                 375                 380

Met Arg Arg Ala Ala Lys Thr Ile Asn Phe Gly Val Leu Tyr Gly Met
385                 390                 395                 400

Ser Ala His Arg Leu Ser Gln Glu Leu Ala Ile Pro Tyr Glu Glu Ala
                405                 410                 415

Gln Ala Phe Ile Glu Arg Tyr Phe Gln Ser Phe Pro Lys Val Arg Ala
            420                 425                 430

Trp Ile Glu Lys Thr Leu Glu Glu Gly Arg Arg Arg Gly Tyr Val Glu
            435                 440                 445

Thr Leu Phe Gly Arg Arg Arg Tyr Val Pro Asp Leu Glu Ala Arg Val
450                 455                 460
```

```
Lys Ser Val Arg Glu Ala Ala Glu Arg Met Ala Phe Asn Met Pro Val
465                 470                 475                 480

Gln Gly Thr Ala Ala Asp Leu Met Lys Leu Ala Met Val Lys Leu Phe
                485                 490                 495

Pro Arg Leu Glu Glu Met Gly Ala Arg Met Leu Leu Gln Val His Asp
                500                 505                 510

Glu Leu Val Leu Glu Ala Pro Lys Glu Arg Ala Glu Ala Val Ala Arg
            515                 520                 525

Leu Ala Lys Glu Val Met Glu Gly Val Tyr Pro Leu Ala Val Pro Leu
            530                 535                 540

Glu Val Glu Val Gly Ile Gly Glu Asp Trp Leu Ser Ala Lys Glu
545                 550                 555
```

THERMOSTABLE POLYMERASE

TECHNICAL FIELD

The field of this invention is DNA polymerases.

BACKGROUND OF THE INVENTION

Polymerases are enzymes that catalyze the formation of polymers from monomers. Thus, DNA polymerases are enzymes that synthesize deoxyribonucleic acid (DNA) from deoxynucleotide triphosphates. DNA dependent DNA polymerases are enzymes that use DNA as a template to synthesize DNA, and as such are critical to biological processes, including DNA replication.

DNA polymerases also find use in a variety of microbiological applications, such as sequencing, in vitro polynucleotide synthesis, and the like. With the advent of the polymerase chain reaction and the multitude of applications based thereon, the use of DNA polymerases has increased dramatically.

Of particular interest to the academic and industrial communities are thermostable polymerases capable of retaining their polymerase activity through the significant temperature modulations that characterize the polymerase chain reaction. A variety of different naturally occurring thermostable polymerases have been isolated and characterized to date. Typically such thermostable polymerases are isolated from prokaryotic hosts which live in climates characterized by high temperature, e.g. natural hot springs, volcanic vents and the like. Representative naturally occurring thermostable polymerases include: *Thermus aquaticus* DNA polymerase; *Thermus thermophilus* DNA polymerase; *Thermococcus litoralis* DNA polymerase; *Thermotoga maritima* DNA polymerase; *Pyrococcus furiosus* DNA polymerase; and the like.

In addition to their polymerase activity, naturally occurring DNA polymerases from bacterial hosts typically also exhibit 5'-exonuclease activity. For many academic and industrial applications, this exonuclease activity is undesirable. As such, a number of synthetic polymerases, e.g. truncation or deletion mutants of naturally occurring polymerases, have been developed which exhibit reduced exonuclease activity as compared to their naturally occurring counterparts.

In view of the ever increasing use of the polymerase chain reaction in today's academic and industrial communities, there continues to be interest in the identification of new thermostable enzymes that exhibit polymerase activity.

RELEVANT LITERATURE

U.S. Patents describing isolated *Thermus aquaticus* DNA polymerase as well as mutants thereof include: U.S. Pat. Nos. 4,889,818; 5,352,600; 5,079,352; 5,405,774; 5,436,149; 5,446,591; 5,445,170; 5,556,772; 5,616,494; and 5,674,738.

U.S. Patents describing other naturally occurring DNA polymerases or mutants thereof include: U.S. Pat. Nos. 4,942,130; 4,946,786; 5,192,674; 5,210,036; 5,332,785; 5,374,553; 5,420,029; 5,489,523; 5,506,137; 5,545,552; 5,618,711 and 5,624,833.

SUMMARY OF THE INVENTION

A novel thermostable enzyme having polymerase activity and substantially no associated nuclease activity is provided. The subject enzyme is characterized by having a region of nine residues at least proximal to the N-terminus in which the nine residues have an amino acid sequence which has less than 50% but greater than 40% amino acid sequence identity with residues 280 to 288 of naturally occurring or wild type *Thermus aquaticus* polymerase. The subject enzyme finds use in a variety of different applications in which polynucleotides are enzymatically produced, particularly polymerase chain reaction (PCR) based applications.

BRIEF DESCRIPTION OF THE FIGURES

FIG. 1 provides the nucleic acid sequence of a polymerase according to a first embodiment of the subject invention.

FIG. 2 provides the amino acid sequence of the polymerase encoded by the nucleic acid sequence of FIG. 1.

FIG. 3 provides the nucleic acid sequence of a polymerase according to a second embodiment of the subject invention.

FIG. 4 provides the amino acid sequence of the polymerase encoded by the nucleic acid sequence of FIG. 2.

DESCRIPTION OF THE SPECIFIC EMBODIMENTS

A thermostable enzyme having polymerase activity and substantially no associated nuclease activity is provided. The subject enzyme is characterized by having a region of nine amino acid residues at least proximal to the N-terminus in which the amino acid sequence of the nine residues has less than 50% but greater than 40% amino acid sequence identity with the amino acid sequence of residues 280 to 288 of naturally occurring *Thermus aquaticus* polymerase. The subject enzyme finds use in a variety of applications in which polynucleotides are enzymatically produced, particularly polymerase chain reaction (PCR) based applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a" "an," and "the" include plural reference unless the context clearly dictates otherwise. Unless defined otherwise, all technical and scientific terms used herein have the same meaning as commonly understood to one of ordinary skill in the art to which this invention belongs.

The Thermostable Enzyme

Thermostable enzymes of the subject invention are characterized by having substantial polymerase activity, specifically DNA dependent DNA polymerase activity, but substantially no nuclease activity. Since the enzymes have substantial polymerase activity, they are capable of catalyzing the synthesis of DNA from deoxynucleotide triphosphates using a DNA strand as a template. Since the subject polymerases lack nuclease activity, they are incapable of catalyzing the hydrolysis of the phosphodiester bonds of DNA polymers. By substantial polymerase activity is meant that the polymerase activity of the enzyme is at least about 80,000 units/mg protein. (Polymerase activity is determined by incubating 5 µl of diluted enzyme fractions with 5 µg of activated calf thymus DNA (Worthington, Freehold, N.J.) in a buffer containing 25 mM TAPS-KOH pH 9.3, 50 mM KCL, 5 mM $MgCl_2$, 1.4 mM β-mercaptoethanol, 200 µM each dNTP and $\alpha$-$^{32}$P dCTP (30–80 cpm/pmol) for 10 min at 72° C. in a total volume of 50 µl. The reaction is terminated by addition of 10 µl of 60 mM EDTA, and the products are precipitated by the addition of 100 µl of 20% trichloroacetic acid and incubation on ice for 15 min. The acid-insoluble product is then separated from the acid soluble nucleotides by filtration through GF/C filters. One unit represents conversion of 10 nmol of nucleotides in 30 min at 72° C.) By thermostable is meant that the enzyme maintains its polymerase activity at temperatures at least in excess of 70° C.

The subject enzyme has a molecular weight that is less than the molecular weight of naturally occurring or wild type *Thermus aquaticus* polymerase. The molecular weight of the subject polymerase ranges from about 60 to 70 kDal, usually from about 62 to 68 kDal, and more usually from about 64 to 68 kDal, as measured by SDS-PAGE electrophoresis. The subject enzyme has an amino acid sequence in which the C-terminal portion is substantially identical to the carboxy domain of the naturally occurring *Thermus aquaticus* DNA polymerase as reported in Lawyer et al., J. Biol. Chem (1989) 264:6427 and having a Genbank accession no J04639, particularly amino acid residues 289 to 832 of the naturally occurring *Thermus aquaticus* DNA polymerase. By substantially identical or the same is meant that the C-terminal portion of subject enzyme, which is from about 530 to 550 amino acids in length, usually from about 540 to 550 amino acids in length and more usually 540 to 545 amino acids in length, where in many instances it is 543 amino acids in length, has an amino acid sequence that has a sequence identity of at least about 90%, usually at least about 95% and more usually at least about 99%, with residues 289 to 832 of the amino acid sequence of naturally occurring *Thermus aquaticus* polymerase, as measured using the BLAST algorithm, as described in Altschul et al., (1990) J. Mol. Biol. 215: 403–410 (using the published default settings). In many embodiments of the subject invention, the C-terminal 543 amino amino acid residues, e.g. 10 to 553, 17 to 560, etc, depending on the particular embodiment of the invention, of the subject enzyme are identical to residues 289 to 832 of wild type *Thermus aquaticus* polymerase. Where the amino acid sequence of the C-terminal domain of the subject enzymes does differ from residues 289 to 832 of the naturally occurring sequence, the difference is not one that significantly provides for a significantly reduced polymerase activity or specificity as compared that observed for the wild type enzyme, where any reduced polymerase activity will not exceed a 4-fold reduction, and usually will not exceed a 2 to 3 fold reduction.

Adjacent to the C-terminal domain described above is the N-terminal domain of the enzyme. The N-terminal domain at least comprises a sequence of nine amino acid residues that has less than 50% but at least 40% amino acid sequence identity with residues 280 to 288 of naturally occurring *Thermus aquaticus* polymerase, as measured using the BLAST algorithm described above, where the number of amino acid residues in the N-terminal domain that are identical with residues 280 to 288 is usually four.

Generally, the sequence of this nine residue domain is:

MRGHEX$_1$GLX$_2$ wherein X$_1$ and X$_2$ are hydrophilic residues, more specifically, polar uncharged hydrophilic residues. X$_1$ is usually either threonine or serine, and in many preferred embodiments is serine. X$_2$ is usually either asparagine or glutamine, and in many preferred embodiments is glutamine.

The above nine residue domain is at least proximal to the N-terminus of the enzyme, where by at least proximal is meant that it is located within at 15 residues of the N-terminus, usually within at least 10 residues of the N-terminus, and preferably within at least 8 residues of the N-terminus. In many embodiments, the first amino acid residue of the above sequence is the N-terminal amino acid residue of the enzyme, i.e. the above nine-residue sequence consists of the first N-terminal acid acids of the enzyme.

In those embodiments of the subject invention in which the above nine residue domain is proximal to the N-terminus by does not make up the N-terminus of the enzyme, the N-terminal leader domain adjacent to the first amino acid residue of the above nine residue domain will have from 1 to 15, usually 1 to 10 and more usually 1 to 8 residues, where in a preferred embodiment, the N-terminal leader domain has a sequence of 6 or 7 residues in length, depending on whether an N-terminal methionine is present or has been post-translationally removed during enzyme synthesis, depending on the particular method used to synthesize the enzyme, as discussed in greater detail below. This N-terminal leader domain may have any sequence, so long as the domain does not adversely effect the polymerase activity or specificity of the enzyme. In many instances, this N-terminal leader domain may have a sequence found in a vector.

In a preferred embodiment in which the nine residue domain is proximal to the N-terminus and a distinct N-terminal leader domain of 6 amino acid residues is present, the first 15 N-terminal residues of the enzyme are:

TMITNSMRGHEX$_1$GLX$_2$ wherein X$_1$ and X$_2$ are as defined above.

In certain embodiments, the subject enzyme has, in addition to the above specified domains and residues, an N-terminal methionine residue, which may or may not be present depending on the host used to produce the enzyme, e.g. in certain hosts this N-terminal methionine residue may be removed through post-translational modification.

In a first preferred embodiment, the enzyme has the amino acid sequence shown in FIG. 2 and identified as SEQ ID NO:02. In a second preferred embodiment, the enzyme has the sequence shown in FIG. 4 and identified as SEQ ID NO:04.

Nucleic Acid Compositions

Also provided by the subject invention are nucleic acid compositions encoding the subject enzymes, as well as fragments of these nucleic acid compositions. By nucleic acid composition is meant a composition comprising a sequence of DNA having an open reading frame that encodes the subject enzyme and is capable, under appropriate conditions, of being expressed as the subject enzyme. A first preferred nucleic acid of the subject invention has the nucleotide sequence shown in FIG. 1 and assigned SEQ ID NO:01. A second preferred nucleic acid of the subject invention has the nucleotide sequence shown in FIG. 3 and assigned SEQ ID NO:03.

Also provided are nucleic acids that are homologous or substantially similar or identical to the nucleic acid shown in FIG. 1 or FIG. 3. By homologous, substantially similar or identical is meant a nucleic acid sequence that has at least 75% sequence identity, usually at least 90%, more usually at least 95% with the sequence shown in FIG. 1 or FIG. 3 as determined using a reference sequence of at least about 18 nt long, more usually at least about 30 nt long, and up to and including the complete sequence that is being compared, where sequence identity is determined using the BLAST algorithm, as described in Altschul et al. (1990), *J. Mol. Biol.* 215:403–10 (using the published default settings).

Also provided are fragments of the above nucleic acid compositions. The fragments may be double or single stranded fragments. The fragments may be obtained from the full length sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Of interest are such fragments that are capable of hybridizing to the DNA under stringent conditions (e.g. at 50° C. or higher and 0.1XSSC (15 mM sodium chloride/01.5 mM sodium citrate)), as such fragments can be used as probes, where fragments that are capable of hybridizing to the 5' end of the nucleic acid which encodes at least a portion of the N-terminal first nine amino acid residues of the subject enzymes are of particular interest.

Preparation of the Subject Enzyme

The subject enzymes can be prepared using any convenient methodology, where methodologies that may be employed typically include preparation of the a nucleic acid encoding the subject enzyme, introduction of the enzyme into a vector for expression, transformation of a host cell with the vector, and expression and recovery of the enzyme. A variety of protocols for accomplishing each of the above steps are well known in art. See Sambrook, Fritsch & Maniatis, Molecular Cloning, A Laboratory Manual (Cold Spring Harbor Press, Inc.) (1989).

Nucleic acids encoding the subject enzymes can be prepared in a number of different ways. For example, the nucleic acid may be synthesized using solid phase synthesis techniques, where the nucleic acid may be synthesized in piecemeal fashion and the synthesized fragments ligated together to produce the final nucleic acid. Alternatively, the 5' region of the nucleic acid that encodes the N-terminal portion of the enzyme may be synthesized and ligated to the remainder of the nucleic acid that has been isolated from the wild type gene. A preferred method for preparing nucleic acids that encode for the subject enzyme is to use the polymerase chain reaction, in which appropriate primers are employed to produce a PCR product using the wild type gene as a template. Appropriate primers for use in this method will introduce the desired coding mutations at the 5' end of the sense strand in the PCR product. In addition, the primers will also preferably provide for the presence of restriction sites, which sites provide for the production of specific ends for subsequent introduction of the PCR product into a vector. Representative primers that find use in this particular method are those identified infra as SEQ ID NO:05 and SEQ ID NO:06.

Following preparation of the nucleic acid, the nucleic acid is then introduced into an expression cassette comprising a nucleic acid encoding the subject polymerase in operational combination with transcriptional initiation and termination regions, which provides for expression of the nucleic acid into the subject enzyme under suitable conditions. Generally, the expression cassette will be present on an expression vector, where the expression vector may be a plasmid that provides for expression of the encoded enzyme under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and ColE1. Expression vectors generally have convenient restriction sites located near the promoter sequence to provide or the insertion of nucleic acid sequences encoding heterologous proteins. In addition, the xpression vector will also typically comprise a gene which provides a marker for detection of the clones that have been transformed with the vector. A variety of markers are known and may be present on the vector, where such markers include those that confer antibiotic resistance, e.g. resistance to ampicillin, tetracycline, chloramphenicol, kanamycin, markers that provide for histochemical detection, etc. Specific vectors that may find use in the subject methods include: pBR322, pUC18, pUC19, πAN13, and the like. Introduction of the nucleic acid encoding the subject enzyme into the expression vector is accomplished by cutting the expression vector and the PCR product with appropriate restriction enzymes and combining the cut fragments under conditions suitable for ligation of the nucleic acid with the expression vector to occur, where such conditions are well known to those of skill in the art.

Following preparation of the expression vector comprising the nucleic acid, the expression vector will be introduced into an appropriate host cell for production of the enzyme, i.e. a host cell will be transformed with the expression vector. Transformation of host cells may be accomplished in any convenient manner, where two representative means of transformation are treatment with divalent cation transformation compositions and electrotransformation. In transformation through divalent cation treatment, the host cells are typically incubated with the one or more divalent cations, e.g. $CaCl_2$, which serves to make the host cell permeable to the vector DNA. See Cohen et al, Proc. Nat'l. Acad. Sci. USA (1972) 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al., Nucleic Acids Research (1988) 16:6127.

A variety of host cells are suitable and may be used in the production of the enzyme, where such host cells may be bacterial cells, yeast cells, or other cells, such as plant cells (see Depicker, J. Mol. Appl. Gen (1982) 1:561, where the host cell will generally be bacterial, e.g. *E. coli B. subtilis, S. cerevisiae*, where an *E. coli* strain is often the host cell of choice. *E. coli* strains that may be used include DH1, DH5, MM294, LE392, MC1061 and JM109.

Following transformation, host cells are screened for incorporation of the expression vector. Transformed colonies, e.g. host cells harboring the expression vector with the nucleic acid encoding the enzyme are identified, and then grown up in large quantity. Where appropriate, agents that induce expression of the enzyme are contacted with the host cell, e.g. isopropylthiogalactoside (IPTG).

Following large scale growth, the expressed enzyme will be harvested and purified for subsequent use. Typically, purification of the enzyme involves disruption of the host cell, inactivation and removal of the native host proteins and precipitation of the nucleic acids. The enzyme is separated from the other host cell constituents using one or more of a number of separation techniques known to those of skill in the art, e.g. centrifugation, dialysis, gel filtration chromatography, ion exchange chromatography, and the like. A typical purification protocol that may be employed exploits the thermostable nature of the subject enzyme as opposed to the naturally occurring proteins of the host cell. Thus, the host cells may be lysed, e.g. by contact with lysozyme, and the resultant cell suspension heated to a temperature that denatures and precipitates the native proteins, e.g. 72° C. The denatured proteins are then removed, e.g. by centrifugation, and the resultant supernatant comprising the enzyme is treated with a nucleic acid precipitating agent, e.g. PEI-cellulose. The supernatant comprising the enzyme may then be further treated to enrich for the enzyme and/or remove other components still present, where a variety of different purification procedures may be employed, where such procedures are described in the patents listed in the Relevant Literature section, supra, the disclosures of which are herein incorporated by reference, as well as in the Guide to Protein Purification (Murray P. Deutscher ed., Harcourt Brace & Co.) (1990). Using these protein purification techniques, isolated enzyme may be prepared, where by isolated is meant a composition that is at least about 95% by weight enzyme, usually at least about 98% by weight enzyme and more usually at least about 99% by weight enzyme, when the composition is dehydrated, e.g. lyophilized.

In addition to the compositions and substantially pure formulations described above, the enzyme may also be present in a composition that is suitable for storage of the enzyme until its intended use, i.e. as a storage stable composition. Storage stable compositions will typically comprise the enzyme in combination with a buffer medium. Buffer mediums of interest typically comprise: buffering agents, e.g. Tris, Tricine, HEPES, phosphate, etc.; solvents, e.g. water, glycerol, etc.; salts, e.g. KCl, NaCl, $(NH_4)_2SO_4$, etc.; reducing agents, e.g. β-mercaptoethanol, DTT, DTE, etc.; chelating agents, e.g. EDTA, CDTA, etc.; detergents, e.g. Triton X100; Tween 20, Thesit, NP40, etc.; and the like.

Utility

The thermostable polymerases of the subject invention find use in a variety of different applications, where such applications include: the polymerase chain reaction (PCR) and protocols based thereon, nucleic acid sequencing, e.g. cycle sequencing, DNA labeling, primer directed mutagenesis, and the like. Various applications, including those listed above, in which the subject enzyme finds use are further described in the U.S. Patents listed in the Relevant Literature section, supra, the disclosures of which are incorporated herein by reference.

The subject polymerase is particularly suited for used in the polymerase chain reaction, and applications based thereon. The polymerase chain reaction (PCR) in which a nucleic acid primer extension product is enzymatically produced from template DNA is well known in the art, being described in U.S. Pat. Nos.: 4,683,202; 4,683,195; 4,800,159; 4,965,188 and 5,512,462, the disclosures of which are herein incorporated by reference.

In such methods, template nucleic acid is first contacted with primer and the subject polymerase under conditions sufficient to enzymatically produce primer extension product. The nucleic acid that serves as template may be single stranded or double stranded, where the nucleic acid is typically deoxyribonucleic acid (DNA), where when the nucleic acid is single stranded, it will typically be converted to double stranded nucleic acid using one of a variety of methods known in the art. The length of the template nucleic acid may be as short as 50 bp, but usually be at least about 100 bp long, and more usually at least about 150 bp long, and may be as long as 10,000 bp or longer, but will usually not exceed 50,000 bp in length, and more usually will not exceed 20,000 bp in length. The nucleic acid may be free in solution, flanked at one or both ends with non-template nucleic acid, present in a vector, e.g. plasmid and the like, with the only criteria being that the nucleic acid be available for participation in the primer extension reaction. The template nucleic acid may be derived from a variety of different sources, depending on the application for which the PCR is being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, mulloses, arthropods, echinoderms, acorn worms, and vertebrates, including reptiles, fishes, birds, snakes, and mammals, e.g. rodents, primates, including humans, and the like. The nucleic acid may be used directly from its naturally occurring source and/or preprocessed in a number of different ways, as is known in the art. In some embodiments, the nucleic acid may be from a synthetic source.

As mentioned above, the template nucleic acid is contacted with primer, the subject polymerase and other reagents into a reaction mixture. The amount of template nucleic acid that is combined with the other reagents will range from about 1 molecule to 1 pmol, usually from about 50 molecules to 0.1 pmol, and more usually from about 0.01 amol to 100 fmol.

The oligonucleotide primers with which the template nucleic acid (hereinafter referred to as template DNA for convenience) is contacted will be of sufficient length to provide for hybridization to complementary template DNA under annealing conditions (described in greater detail below) but will be of insufficient length to form stable hybrids with non-complementary template DNA. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers, depending on whether linear or exponential amplification of the template DNA is desired. Where a single primer is employed, the primer will typically be complementary to one of the 3' ends of the template DNA and when two primers are employed, the primers will typically be complementary to the two 3' ends of the double stranded template DNA.

The subject polymerase may be used as the sole polymerase in the reaction mixture, or combined with one or more additional polymerases as desired, e.g. for the production of long PCR products. Where the subject polymerase is used as the sole polymerase in the reaction mixture, the reaction mixture will typically comprise from about 0.1 U/μl to 1 U/μl of the subject polymerase, usually from about 0.2 to 0.5 U/μl of the subject polymerase, where "U" corresponds to incorporation of 10 nmol dNTP into acid-insoluble material in 30 min at 74° C.

Where the subject polymerase is combined with an additional polymerase, the additional polymerase will generally be a "Family B" polymerase, where the such polymerase are described in Braithwaite & Ito, Nucleic Acids Res. (1993) 21:787–802. Family B polymerases of interest include *Thermococcus litoralis* DNA polymerase (Vent) as described in Perler et al., Proc. Natl. Acad. Sci. USA (1992) 89:5577; Pyrococcus species GB-D (Deep Vent); *Pyrococcus furiosus* DNA polymerase (Pfu) as described in Lundberg et al., Gene (1991) 108:1–6, *Pyrococcus woesei* (Pwo) and the like. Where the subject polymerase is combined with an additional Family B polymerase, the subject polymerase will be present in an amount greater than the Family B polymerase, where the difference in activity will usually be at least 10-fold, and more usually at least about 100-fold. Accordingly, the reaction mixture prepared upon contact of the template DNA, primer, polymerase and other necessary reagents, as described in greater detail below, will typically comprise from about 0.1 U/μl to 1 U/μl of the subject polymerase, usually from about 0.2 to 0.5 U/μl of the subject polymerase, while the amount of Family B polymerase will typically range from about 0.01 mU/μl to 10 mU/μl, usually from about 0.05 to 1 mU/μl and more usually from about 0.1 to 0.5 mU/μl, where "U" corresponds to incorporation of 10 nmol dNTP into acid-insoluble material in 30 min at 74° C. In a preferred embodiment, the subject polymerase will be combined with Deep Vent polymerase, where the ratio of activity of the subject polymerase to Deep Vent will range from 50 to 10,000, more usually from 500 to 1000.

Also present in the reaction mixture will be deoxyribonucleoside triphosphates (dNTPs). Usually the reaction mixture will comprise four different types of dNTPs corresponding to the four naturally occurring bases, i.e. dATP, dTTP, dCTP and dGTP. The reaction mixture will further comprise an aqueous buffer medium which includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micro-ohms. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 2 to 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA and the like and non-ionic detergents, such as Tween 20, Triton X100, NP40, and the like.

In preparing the reaction mixture, the various constituent components may be combined in any convenient order. For example, the buffer may be combined with primer, polymerase and then template DNA, or all of the various constituent components may be combined at the same time to produce the reaction mixture.

Following preparation of the reaction mixture, the reaction mixture is subjected to a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98 and more usually from about 93 to 96° C. for a period of time ranging from about 3 to 120 sec, usually from about 5 to 60 sec.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 50 to 75, usually from about 55 to 70° C. Annealing conditions will be maintained for a period of time ranging from about 15 sec to 60 sec.

Following annealing of primer to template DNA or during annealing of primer to template DNA, the reaction mixture will be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described in U.S. Pat. Nos. 5,612,473; 5,602,756; 5,538,871; and 5,475,610, the disclosures of which are herein incorporated by reference.

The subject polymerase chain reaction methods find use in any application where the production of enzymatically produced primer extension product from template DNA is desired, such as in the generation of specific sequences of cloned double-stranded DNA for use as probes, the generation of probes specific for uncloned genes by selective amplification of particular segments of cDNA or genomic DNA, the generation of libraries of cDNA from small amounts of mRNA, the generation of large amounts of DNA for sequencing, the analysis of mutations, generation of DNA fragments for gene expression, chromosome crawling, and the like. Thus, the subject methods of PCR find use in diagnosis, such as of genetic disorders and identification of pathogens; in genetic identification of forensic samples, in the analysis of mutations, and the like. See PCR, Essential Techniques, (ed J. F. Burke, John Wiley & Sons) (1996).

Kits

Also provided are kits comprising the subject polymerase. The kits according to the present invention include at least the subject thermostable enzyme, where the enzyme may be provided in substantially pure form or, more usually, in a storage stable composition, as described above. Also present in the kit may be a second polymerase, such as a Family B polymerase, as described above. The subject kits may further comprise additional reagents which are required for or convenient and/or desirable to include in the depending on the intended use of the kit, where such reagents include an aqueous buffer medium (either prepared or present in its constituent components, where one or more of the components may be premixed or all of the components may be separate), and the like. The various reagent components of the kits may be present in separated containers, or may all be precombined into a reagent mixture for combination with template DNA.

The following examples are offered by way of illustration and not by way of limitation.

Experimental

I. Construction of Plasmids and Overexpression of Taq Polymerase Mutant

PCR was performed with a DNA fragment encoding wildtype Taq polymerase originating from *Thermus aquaticus* strain YT-1 as a template and primers 1 and 2.

Primer 1: (SEQ ID NO:05)
    EcoR1

5'-AAG AAT TCC ATG AGG GGG CAC GAG TCC GGC CTT CAG GAA AGC CCC AAG GC

Met Arg Gly His Glu Ser Gly Leu Gln Glu Ser Pro Lys 283 284 285 286 287 288 289 290 291 292

Primer 2: (SEQ ID NO:06)
    XbaI

5'-ATT CTA GAG GTG GTA TCA CTC CTT GGC GGA G

The resulting PCR product was purified and treated with restriction nucleases EcoRI and XbaI to create specific DNA ends. The fragment was ligated into the corresponding sites of pUC18 (Yanisch-Perron, et al., Gene (1985) 33:103–119). The construct was introduced in E. coli strain JM109 (Yanisch-Perron, supra) and a clone containing the desired plasmid (pClonTaq) was established. The mutant Taq polymerase gene was sequenced to confirm the absence of any unwanted mutations, and the sequence is shown in FIG. 3. The amino acid sequence for the enzyme is shown in FIG. 4.

For overexpression, the clone was grown at 37° C. in LB medium containing 100 µg/ml ampicillin. IPTG was added at OD600 of 0.3 to a final concentration of 0.5 mM and the culture was further grown for 18 hr. The cells were recovered by centrifugation and stored at −80° C.

It is evident from the above results and discussion that a novel thermostable polymerase is provided that finds use in a variety of different applications. The subject thermostable enzyme provides for desirable characteristics with respect to stability with respect to proteolysis and/or thermal inactivation, and enhanced solubility in hydrophilic, e.g. aqueous solvents.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

---

What is claimed is:

1. A thermostable enzyme having polymerase activity and substantially no nuclease activity, where the amino acid sequence of said enzyme comprises a sequence of nine amino acid residues at least proximal to the N-terminus of the enzyme that has less than 50% but greater than 40% amino acid identity with residues 280 to 288 of naturally occurring *Thermus aquaticus* polymerase.

2. The thermostable enzyme according to claim 1, wherein the number of amino acid residues in said sequence of nine amino acid residues that are identical to the residues of said residues 280 to 288 of naturally occurring *Thermus aquaticus* polymerase is four.

3. The thermostable enzyme according to claim 1, wherein said nine amino acid residues are:

MRGHEX$_1$GLX$_2$ wherein X$_1$ and X$_2$ are hydrophilic residues.

4. The thermostable enzyme according to claim 1, wherein said enzyme has a molecular weight ranging from about 60 to 70 kDal as measured by SDS-PAGE.

5. The thermostable enzyme according to claim 1, wherein the C-terminal portion of said enzyme has an amino acid sequence that is substantially the same as the amino acid sequence of naturally occurring *Thermus aquaticus* polymerase.

6. A thermostable enzyme having polymerase activity and substantially no nuclease activity, wherein the N-terminal domain of said enzyme comprises a sequence of nine amino acid residues at least proximal to the N-terminus, wherein said nine amino acid residues are:

MRGHEX$_1$GLX$_2$ wherein X$_1$ and X$_2$ are hydrophilic residues.

7. The thermostable enzyme according to claim 6, wherein said hydrophilic residues are polar and uncharged.

8. The thermostable enzyme according to claim 7, wherein said X$_1$ is selected from the group consisting of threonine and serine.

9. The thermostable enzyme according to claim 7, wherein said X$_2$ is selected from the group consisting of asparganine and glutamine.

10. The thermostable enzyme according to claim 6, wherein the C-terminal portion of said enzyme has an amino acid sequence that is substantially the same as the amino acid sequence of naturally occurring *Thermus aquaticus* polymerase.

11. The thermostable enzyme according to claim 10, wherein said enzyme is 553 residues long and the amino acid sequence of residues 10 to 553 is substantially the same as residues 289 to 832 of the naturally occurring *Thermus aquaticus* polymerase.

12. The thermostable enzyme according to claim 10, wherein said enzyme is 560 residues long and the amino acid sequence of residues 17 to 560 is substantially the same as residues 289 to 832 of the naturally occurring *Thermus aquaticus* polymerase.

13. A thermostable enzyme having polymerase activity and substantially no nuclease activity, wherein said enzyme is 553 amino acid residues long, wherein the nucleotide sequence of residues 1 to 9 is:

MRGHEX$_1$GLX$_2$ wherein X$_1$ and X$_2$ are polar uncharged residues; and
the amino acid sequence of residues 10 to 553 is substantially the same as residues 289 to 832 of the naturally occurring *Thermus aquaticus* polymerase.

14. The thermostable enzyme according to claim 13, wherein X$_1$ is serine.

15. The thermostable enzyme according to claim 13, wherein X$_2$ is glutamine.

16. A thermostable polymerase having the amino acid sequence of SEQ ID NO:02.

17. A thermostable enzyme having polymerase activity and substantially no nuclease activity, wherein said enzyme is 560 amino acid residues long, wherein the nucleotide sequence of residues 1 to 15 is:

TMITNSMRGHEX$_1$GLX$_2$ wherein X$_1$ and X$_2$ are polar uncharged residues; and
the amino acid sequence of residues 16 to 560 is substantially the same as residues 289 to 832 of the naturally occurring *Thermus aquaticus* polymerase.

18. The thermostable enzyme according to claim 17, wherein X$_1$ is serine.

19. The thermostable enzyme according to claim 17, wherein X$_2$ is glutamine.

20. A thermostable polymerase having the amino acid sequence of SEQ ID NO:04.

21. A nucleic acid having a nucleotide sequence encoding the thermostable enzyme according to claim 1.

22. A nucleic acid according to claim 21, wherein said nucleic acid has a nucleic acid sequence that is substantially identical to the nucleotide sequence of SEQ ID NO:01 or SEQ ID NO:03.

23. A fragment of the nucleic acid according to claim 21.

24. An isolated nucleic acid or mimetic thereof that hybridizes under stringent conditions to the nucleic acid according to claim 21 or its complementary sequence.

25. An expression cassette comprising a transcriptional initiation region functional in an expression host, a nucleic acid having a nucleotide sequence found in the nucleic acid according to claim 21 under the transcriptional regulation of said transcriptional initiation region, and a transcriptional termination region functional in said expression host.

26. A cell comprising an expression cassette according to claim 25 as part of an extrachromosomal element or integrated into the genome of a host cell as a result of introduction of said expression cassette into said host cell.

27. The cellular progeny of the host cell according to claim 26.

28. A method of producing the thermostable enzyme according to claim 1, said method comprising:

growing a cell according to claims 26 or 27, whereby said thermostable enzyme is expressed; and isolating said thermostable enzyme substantially free of other proteins.

29. A polymerase composition comprising:

the thermostable enzyme according to claim 1; and at least one additional polymerase.

30. The polymerase composition according to claim 29, wherein said at least one additional polymerase is a Family B polymerase.

31. The polymerase composition according to claim 29, wherein said polymerase is thermostable.

32. The polymerase composition according to claim 29, wherein said polymerase has nuclease activity.

33. The polymerase composition according to claim 29, wherein said polymerase is Deep Vent polymerase.

34. A kit for use in the enzymatic production of polynucleotides, said kit comprising:

the thermostable enzyme according to claim 1.

35. The kit according to claim 34, wherein said kit further comprises dNTPs.

36. The kit according to claim 35, wherein said kit further comprises at least one buffer medium.

37. The kit according to claim 34, wherein said kit further comprises a second polymerase.

* * * * *